(12) United States Patent
Masters et al.

(10) Patent No.: US 11,090,185 B2
(45) Date of Patent: Aug. 17, 2021

(54) OSTOMY APPLIANCE

(71) Applicant: Hollister Incorporated, Libertyville, IL (US)

(72) Inventors: Brock Edward Masters, Des Plaines, IL (US); Paul Charles Fletter, Mt. Prospect, IL (US); Mark W. Jockel, Chicago, IL (US); Jeremy Robert Quint, Round Lake Beach, IL (US)

(73) Assignee: Hollister Incorporated, Libertyville, IL (US)

( * ) Notice: Subject to any disclaimer, the term of this patent is extended or adjusted under 35 U.S.C. 154(b) by 537 days.

(21) Appl. No.: 15/969,488

(22) Filed: May 2, 2018

(65) Prior Publication Data

US 2018/0250157 A1 Sep. 6, 2018

Related U.S. Application Data

(63) Continuation of application No. 14/237,541, filed as application No. PCT/US2012/047177 on Jul. 18, 2012, now Pat. No. 9,993,363.

(60) Provisional application No. 61/521,605, filed on Aug. 9, 2011.

(51) Int. Cl.
| | |
|---|---|
| *A61F 5/445* | (2006.01) |
| *A61F 5/441* | (2006.01) |
| *A61F 5/44* | (2006.01) |

(52) U.S. Cl.
CPC .............. *A61F 5/445* (2013.01); *A61F 5/441* (2013.01); *A61F 5/4404* (2013.01); *A61F 5/4405* (2013.01); *A61F 5/4407* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,875,451 | A * | 3/1959 | Stegeman | A61G 9/006 4/144.1 |
| 3,523,534 | A * | 8/1970 | Nolan | A61F 5/445 604/335 |
| 3,724,461 | A * | 4/1973 | Eisenberg | A61M 3/0245 604/262 |
| 3,825,005 | A * | 7/1974 | Fenton | A61F 5/4407 604/335 |
| 4,280,498 | A * | 7/1981 | Jensen | A61F 5/4405 251/310 |
| 4,411,659 | A * | 10/1983 | Jensen | A61F 5/441 604/332 |

(Continued)

FOREIGN PATENT DOCUMENTS

| | | |
|---|---|---|
| GB | 2116433 A | 9/1983 |
| GB | 2139501 A | 11/1984 |

(Continued)

OTHER PUBLICATIONS

International Preliminary Report on Patentability for PCT/US2012/047177 dated Feb. 11, 2014.

*Primary Examiner* — Guy K Townsend
(74) *Attorney, Agent, or Firm* — Levenfeld Pearlstein, LLC

(57) ABSTRACT

An ostomy appliance includes a dual-chamber pouch, which can continuously drain liquids from body waste, while collecting solids in the pouch. The ostomy appliance can also include a flat output tap including a lumen, the size of which can be increased by applying pressure.

12 Claims, 4 Drawing Sheets

(56) References Cited

U.S. PATENT DOCUMENTS

| | | | | |
|---|---|---|---|---|
| 4,592,750 A | * | 6/1986 | Kay | A61F 5/4404 604/277 |
| 4,596,566 A | * | 6/1986 | Kay | A61F 5/445 604/176 |
| 4,668,227 A | * | 5/1987 | Kay | A61B 90/70 134/57 R |
| D295,220 S | * | 4/1988 | Kay | A61F 5/441 D24/121 |
| 5,085,652 A | * | 2/1992 | Johnsen | A61F 5/441 604/333 |
| 5,306,264 A | * | 4/1994 | Ferguson | A61F 5/441 604/333 |
| 5,348,546 A | * | 9/1994 | Norton | A61F 5/445 604/332 |
| 5,356,400 A | * | 10/1994 | Temple | A61B 10/0038 604/327 |
| 5,690,623 A | * | 11/1997 | Lenz | A61F 5/441 604/332 |
| 5,698,623 A | * | 12/1997 | Jacobs | C08G 18/324 252/514 |
| 5,745,926 A | * | 5/1998 | Cailleteau | A61F 5/44 383/44 |
| 5,772,644 A | * | 6/1998 | Bark | A61B 10/0096 600/573 |
| D396,731 S | * | 8/1998 | Mirto | A61F 5/441 D24/118 |
| 6,032,831 A | * | 3/2000 | Gardner | A45F 3/16 220/703 |
| 7,306,581 B2 | | 12/2007 | Falconer et al. | |
| 7,476,220 B2 | * | 1/2009 | Lillegaard | A61F 5/4404 4/144.2 |
| 7,879,015 B2 | | 2/2011 | Villefrance et al. | |
| 7,879,016 B2 | * | 2/2011 | Mandzij | A61F 5/4407 604/335 |
| 2004/0049837 A1 | * | 3/2004 | Falconer | A61F 5/4407 4/144.1 |
| 2005/0131360 A1 | * | 6/2005 | Villefrance | A61F 5/445 604/332 |
| 2007/0265588 A1 | * | 11/2007 | Pedersen | A61F 5/4407 604/337 |
| 2008/0033379 A1 | * | 2/2008 | Pedersen | A61F 5/4407 604/335 |
| 2014/0194843 A1 | * | 7/2014 | Masters | A61F 5/4405 604/333 |

FOREIGN PATENT DOCUMENTS

| | | |
|---|---|---|
| GB | 2265832 A | 10/1993 |
| JP | S63189217 U | 12/1988 |
| JP | S64500487 A | 2/1989 |
| JP | 2007082697 A | 4/2007 |
| WO | 8706823 A1 | 11/1987 |

* cited by examiner

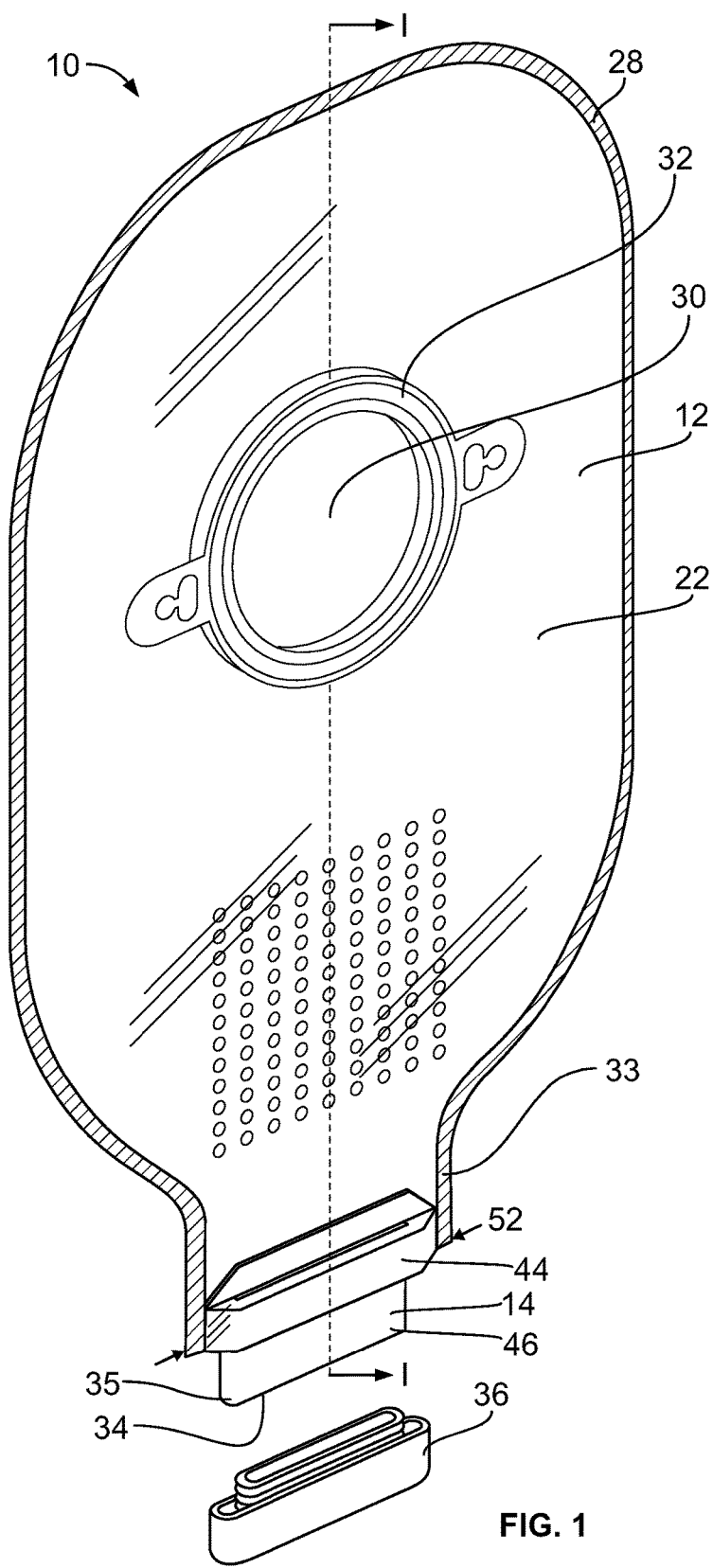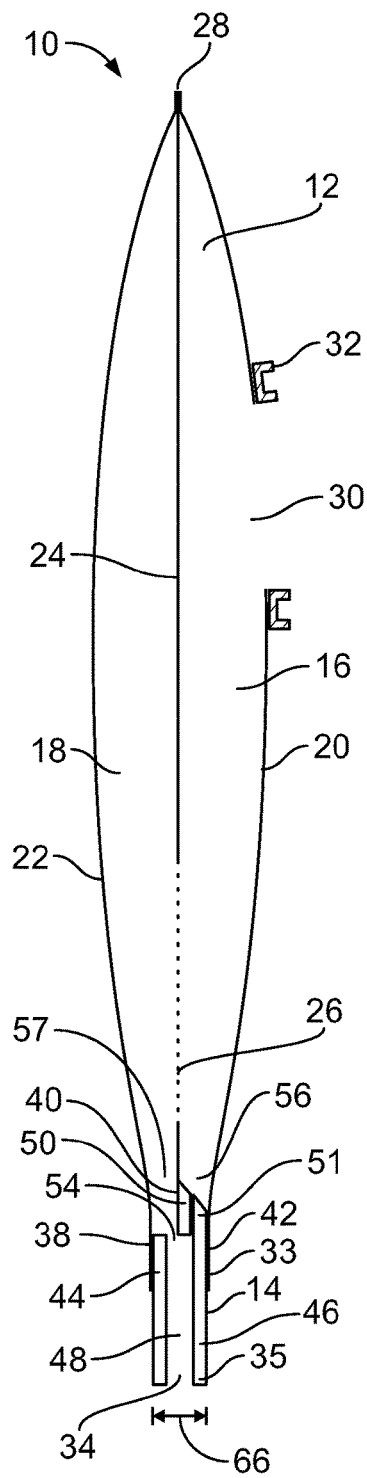
FIG. 1
FIG. 2

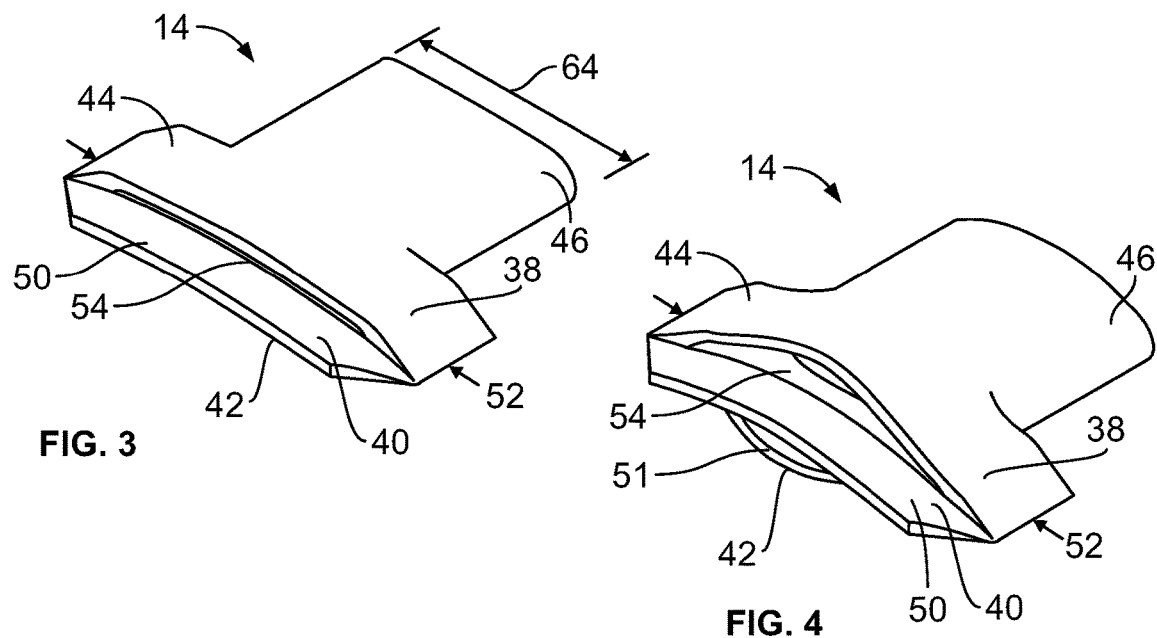
FIG. 3
FIG. 4
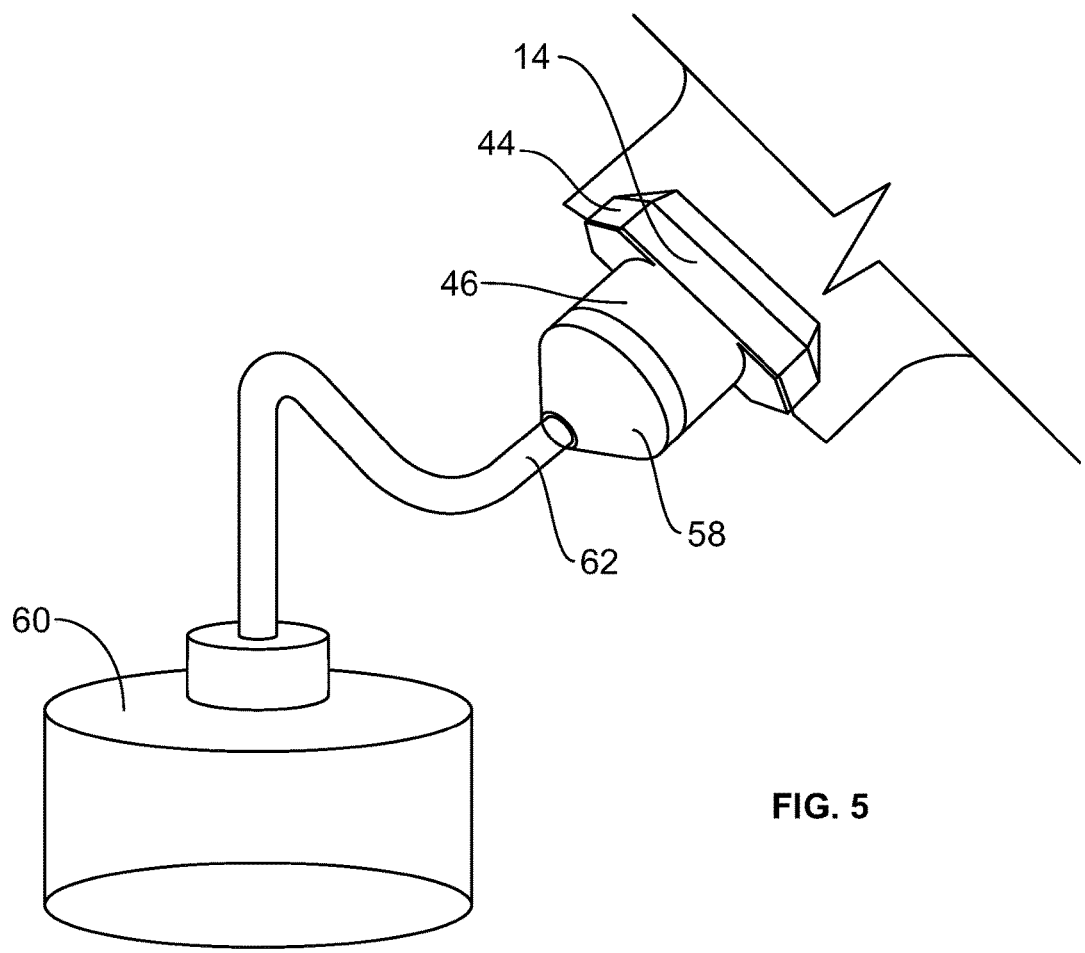
FIG. 5

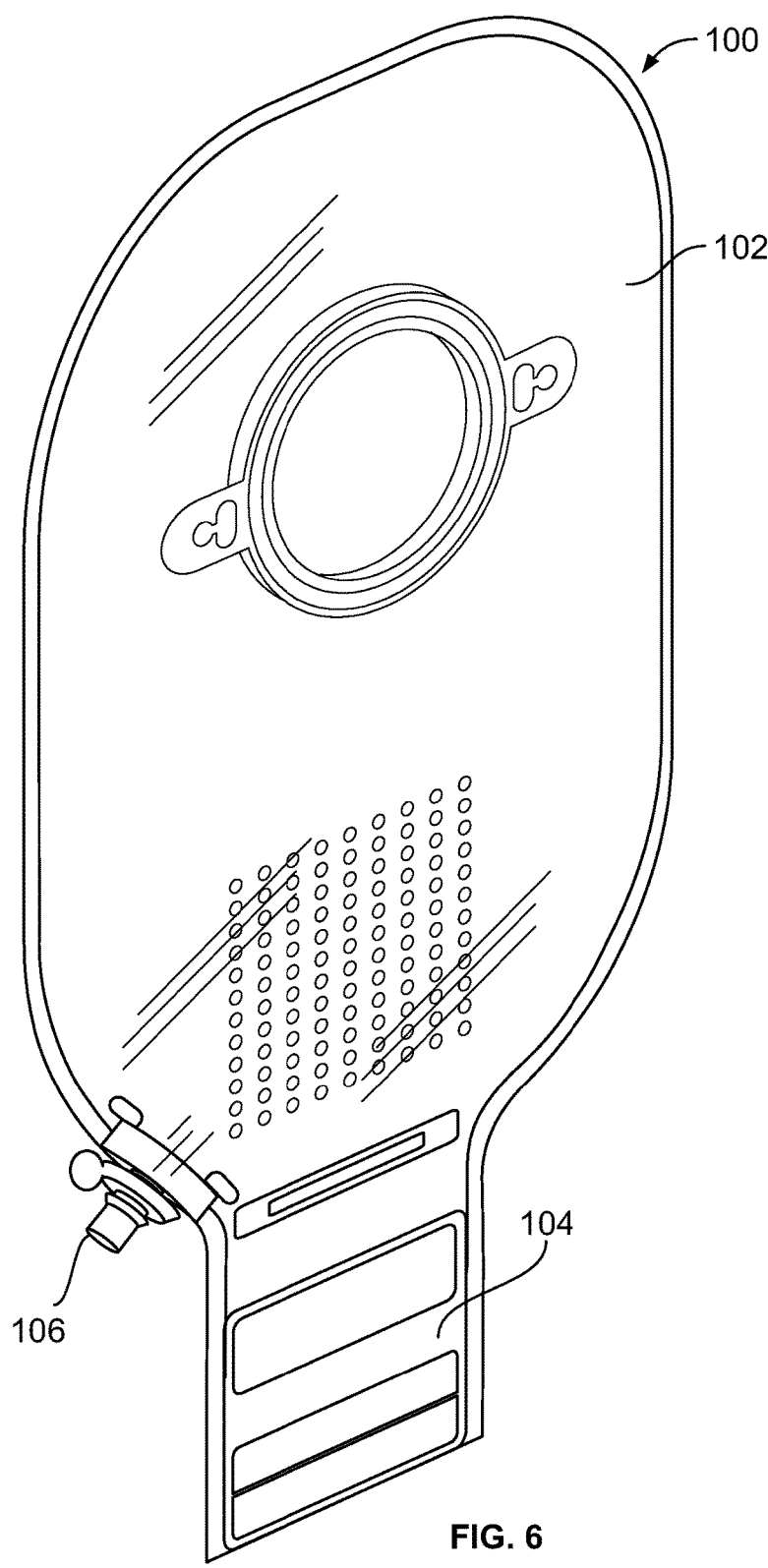
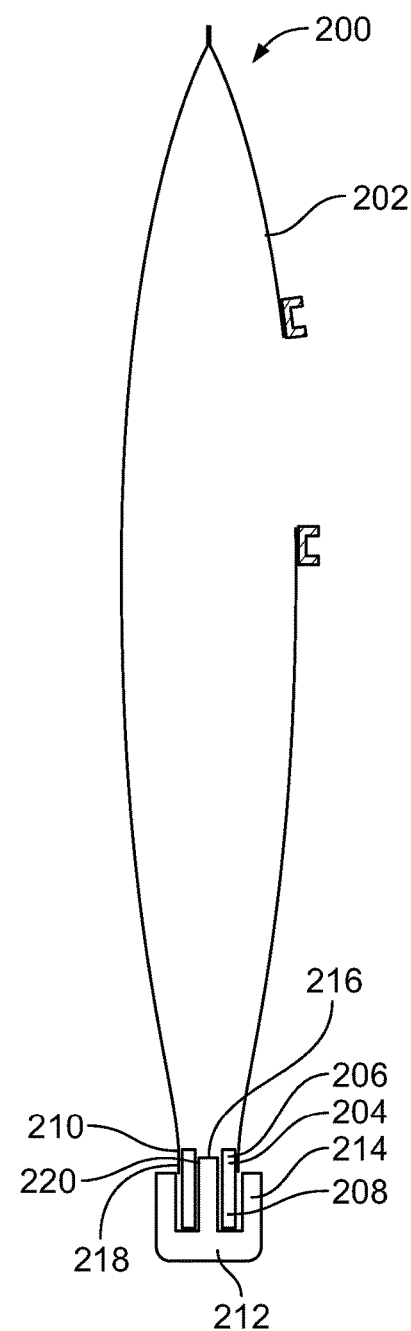
FIG. 6
FIG. 7

OSTOMY APPLIANCE

CROSS-REFERENCE TO RELATED APPLICATION DATA

This application is a continuation of U.S. patent application Ser. No. 14/237,541 which is a 371 application of PCT/US2012/047177, filed Jul. 18, 2012, which claims the benefit and priority of provisional U.S. Patent Application No. 61/521,605, filed Aug. 9, 2011, the disclosures of which are incorporated herein by reference in their entirety.

BACKGROUND

The present disclosure relates to ostomy appliances, and more particularly to a dual-chamber ostomy pouch and a flat output tap for ostomy appliances.

Ostomy pouches for the collection of body waste output from a stoma are well known. Ostomy pouches typically include flat, opposing side walls secured together along their edges to define a human stomal discharge collection cavity. One of the side walls is provided with an opening to receive a stoma, and means such as a connecting flange is provided for securing the pouch to an adhesive barrier placed to surround the stoma so that body waste discharged through the stoma will be received within the cavity. At its lower end, the ostomy pouch may have a discharge opening which may be closed during collection of body waste that passes through the stoma but may be opened for draining the body waste from the pouch after a period of use. Alternatively, the ostomy pouch may be designed for a single use in which case it will not be provided with a discharge opening since the entire pouch will be discarded after it has substantially filled with human stomal discharge.

A drainable pouch is typically reusable following periodic emptying of the body waste by utilizing a closure for the discharge opening. Such closures may take a number of different forms so long as it serves to prevent leakage of the body waste. On the other hand, there is no need for a closure in the case of a single use pouch since it is intended to be discarded following a single use.

Some drainable pouches are designed to be coupled to drainage tubes leading to relatively large volume bedside containers. These permit stoma discharge to drain continuously through the pouch into the container so that, for example, the user can sleep through the night without periodic need to empty the contents of the ostomy pouch. Such drainable pouches include an output tap for connecting to a drainage tube, either directly or via an adapter. Output taps typically have a generally cylindrical shape and a circular cross-sectional area. They are bulky under clothing and can have difficulty passing large pieces of solid matters. This can often lead to user discomfort and clogged night time drainage systems.

Accordingly, there is a need for an improved ostomy appliance. Desirably, such an ostomy appliance can separate solid matter from liquid waste. More desirably, such an appliance includes an outlet that can discharge liquid waste separate from or in conjunction with solid waste from the ostomy pouch.

BRIEF SUMMARY

Drainable ostomy pouches, which can connect to an external container for continuous drainage of pouch contents have been used for ostomy patients. Particularly, ileostomy patients have used high output drainable ostomy pouches, which include an output tap for draining stoma discharge, which is typically a mixture of liquids and solids. Output taps for high output drainable pouches typically have a generally cylindrical shape with a circular cross-sectional area, and are formed of a polymeric material that maintains a cylindrical lumen. However, these output taps are bulky under clothing and often become clogged when attached to a night drain collector. This can cause leakage and disrupt a user's sleep.

Thus, an improved ostomy appliance is provided according to various embodiments. In one embodiment, the ostomy appliance includes an ostomy pouch configured to separate solids and liquids in stoma discharge and allow separated liquids to continuously drain while keeping solids in the pouch to reduce the risk of the output tap becoming clogged. In this embodiment, solids are retained in a body side chamber and liquids flow into an outer chamber of the ostomy pouch. The ostomy appliance can include a liquid valve or tap on the outer chamber for connecting to a night drainage container to drain liquids from the outer chamber. Thus, the risk of the valve or tap becoming clogged by solids is significantly reduced or eliminated. The ostomy pouch also includes an outlet, which can be opened to drain all outputs, such as a drainable fold-up type closure.

Alternatively, the ostomy appliance includes a high output tap that has a generally flat profile, which lays flat against the user. Such an output tap is less bulky than conventional high output taps and provides a higher degree of discretion for the user. According to an embodiment, the output tap includes a lumen, the size of which can be increased to accommodate larger solids, thereby reducing a risk of clogging. The output tap includes a closure cap that may fit both inside and outside of a tap outlet to provide a secure, two-location seal when the closure cap is engaged with the tap. In another embodiment, a flat high output tap is configured to connect to a night drainage tube directly or via an adapter to drain liquids from the ostomy pouch. The same flat high output tap can be opened to empty both liquids and solids in the ostomy pouch.

In one aspect, an ostomy appliance including a pouch and a flat output tap is provided. The pouch includes a pouch inlet for receiving body waste from a stoma and a pouch outlet. The flat output tap is attached to the pouch outlet and includes at least one inlet, an outlet, and a lumen, which provides a path for the body waste to flow out of the pouch. The flat output tap is configured such that a size of the lumen is adjustable.

In another aspect, an ostomy appliance includes a pouch, which includes a first chamber and a second chamber, an inlet, at least one outlet, and a filter configured to separate liquids and solids in body waste received via the inlet.

In yet another aspect, an ostomy appliance includes a pouch, which includes a first chamber and a second chamber, a pouch inlet, a pouch outlet, and a flat output tap. The flat output tap is attached to the pouch outlet, and includes at least one inlet, an outlet, and a lumen providing a path for the body waste to flow out of the pouch. The flat output tap is configured such that a size of the lumen is adjustable.

Other aspects, objectives and advantages will become more apparent from the following detailed description when taken in conjunction with the accompanying drawings.

BRIEF DESCRIPTION OF THE SEVERAL VIEWS OF THE DRAWINGS

The benefits and advantages of the present embodiments will become more readily apparent to those of ordinary skill in the relevant art after reviewing the following detailed description and accompanying drawings, wherein:

FIG. 1 is a perspective view of an ostomy appliance including a dual-chamber pouch and a flat output tap according to an embodiment;

FIG. 2 is a cross-sectional illustration of the ostomy appliance of FIG. 1 taken along line I-I;

FIG. 3 is a perspective view of the flat output tap of FIG. 1 in a closed lip position;

FIG. 4 is a perspective view of the flat output tap of FIG. 1 in an open lip position;

FIG. 5 is the ostomy appliance of FIG. 1 connected to a collection container via an adapter and a tube according to an embodiment;

FIG. 6 is a perspective view of an ostomy appliance including a dual-chamber pouch, a fold-up type closure and a liquid valve according to a different embodiment;

FIG. 7 is a cross-sectional illustration of an ostomy appliance including a flat output tap and a closure according to another embodiment;

DETAILED DESCRIPTION

Figure 8:
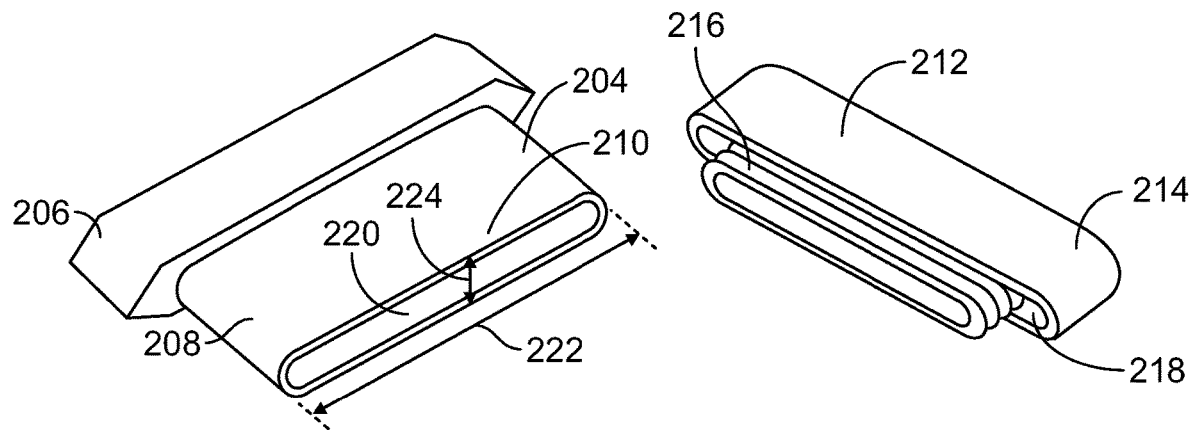
FIG. 8 is a perspective view the flat output tap and closure of FIG. 7 shown with the closure removed from the tap for clarity of illustration.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

Referring now to the figures and in particular to FIGS. 1 and 2, there is shown an ostomy appliance 10 according to an embodiment. The ostomy appliance 10 includes an ostomy pouch 12 and a flat output tap 14. The ostomy pouch 12 is a dual-chamber pouch including a body side chamber 16 and an outer chamber 18. The ostomy pouch 12 includes flat, opposing side walls, namely a body side wall 20 and an outer wall 22, and a center wall 24, which includes a separating or filtering section 26. The opposing side walls 20, 22, and the center wall 24 are secured together along their edges 28, for example via heat sealing, to define the body side chamber 16 and the outer chamber 18.

The body side wall 20 is provided with an inlet opening 30 to receive a stoma, and a pouch side connecting flange 32 for securing the ostomy pouch 10 to an adhesive barrier (not shown) placed around the stoma via a body side connecting flange (not shown) so that body waste material discharged through the stoma is received within the body side chamber 16 of the ostomy pouch 12. Although, this embodiment is shown as a two-piece ostomy appliance including the pouch side connecting flange 32 and the separate adhesive barrier including the body side connecting flange (not shown), in other embodiments, the ostomy appliance may be a one piece pouch, wherein an adhesive skin barrier is directly attached to the pouch.

The filtering section 20 is configured to separate liquids from solids in body waste entering the body side chamber 16 via the inlet opening 30. In one embodiment, the filtering section 20 includes a plurality of openings, for example, a plurality of perforations or slits, to allow liquids to pass through the filtering section into the outer chamber 18, but block solids from passing through the filtering section 20. In the illustrated embodiment, the filtering section 20 includes plurality of circular openings, each opening may have a diameter between about 1 mm and about 5 mm, for example, between about 2 mm and about 4 mm. In other embodiments, the filtering section may have different shape and/or size openings to accommodate different body wastes to effectively separate liquids from solids. For example, the size of the openings may be smaller than 1 mm diameter.

At its lower end, the ostomy appliance 10 includes a tail portion 33. The flat output tap 14 is arranged in the tail portion 33 and is sealingly attached to inner surfaces of the peripheral end of the tail portion 33. A perspective view of the flat output tap 14 is shown in FIG. 3. In this embodiment, the flat output tap 14 is a one-piece tap formed of a flexible, resilient material via a conventional molding process. Suitable materials for the flat output tap 14 include, but not limited to, silicone, rubber, elastomers and the like. As shown in FIGS. 2 and 3, the flat output tap 14 has a generally flat profile, and includes a lumen 48 defining an outlet path for stoma discharge to exit the ostomy pouch 12. The term "generally flat profile" is used herein to describe a shape of the output tap that has a width:thickness ratio of at least 2, wherein the width 64 (FIG. 3) and the thickness 66 (FIG. 2) are measured at the outlet end of the output tap, such that the output tap lays flat when the ostomy appliance is worn by the user to provide the user with a greater degree of discretion when compared to conventional output taps having circular cross-sectional areas.

The flat output tap 14 has a top portion 44, which is configured to fit in the peripheral end of the tail portion 33 of the ostomy pouch 12, and a bottom portion 46 defining a discharge outlet 34. The bottom portion 46 has a flattened cylinder-like shape, such that in a relaxed state, the width 64 (FIG. 3) is greater than the thickness 66 (FIG. 2). In the illustrated embodiment, the width 64 to thickness 66 ratio of the bottom portion 46 is greater than 2, and preferably greater than 4.

The top portion 44 may include three sealing surfaces 38, 40, 42 for sealing against the pouch walls 22, 24, 20. A first sealing surface 38 and a second sealing surface 40 are formed on one side of the flat output tap 14, and a third sealing surface 42 is formed on the opposite side of the output tap 14. The top portion 44 includes a first lip 50 and a second lip 51. The second sealing surface 40 is formed on the first lip 50, and the third sealing surface 42 is formed on the second lip 51. The lips 50, 51 are in contact with each other in a closed lip position as shown in FIGS. 2-3, until pressure is applied along edges 52 of the top portion 44 to open the lips 50, 51, as shown in FIGS. 1, 3, and 4. For example, the user can press edges 52 with his fingers to open the lips 50, 51. FIG. 4 shows the flat output tap 14 in an open position. The lips 50, 51 define an inlet from the body side chamber 16, which remains closed until pressure is applied to open the inlet. An opening 54 arranged between the first sealing surface 38 and the second sealing surface 40 defines a liquid inlet from the outer chamber 18.

The flat output tap 14 is arranged in the tail portion 33 of the ostomy pouch 12 such that the first sealing surface 38 faces an inner surface of the outer wall 22, the second sealing surface 40 faces a body side surface of the center wall 24, and the third sealing surface 42 faces an inner surface of the body side wall 20. As shown in FIG. 2, the first sealing surface 38 is sealingly attached to the inner surface of the outer wall 22. The second sealing surface 40 is sealingly attached to the surface of the center wall 24, which faces the body side chamber 16. The third sealing surface 42 is sealingly attached to the inner surface of the body side wall 20. The sealing surfaces 38, 40, 42 can be attached to the walls 22, 24, 20 using conventional methods, such as heat sealing or adhesives.

Further, the ostomy appliance 10 can include a closure cap 36 (FIG. 1), which may fit both inside and outside of an outlet end portion 35 of the flat output tap 14, to provide a two-location, leak free seal when the closure cap 36 is engaged with the flat output tap 14. The closure cap 36 may be tethered to the flat output tap 14.

In use, the ostomy appliance 10, which is sealingly closed with the closure cap 36, is attached to the adhesive skin barrier (not shown.) Stoma discharge flows in via the opening 30 into the body side chamber 16. The stoma discharge typically includes both liquids and solids. The liquids in the stoma discharge flows into the outer chamber 18 from the body side chamber 16 through the center wall filtering section 26. Thus, the stoma discharge is generally separated into liquids and solids via the filtering section 26.

In FIG. 5, an adapter 58 is engaged with the discharge outlet 34 for draining body waste in the ostomy pouch 12 to a collection container 60 via tube 62. As shown in FIG. 2, an outlet 56 of the body side chamber 16 is closed by the closed lips 50, 51 of the flat output tap 14, which prevents solids in the body side chamber 16 from flowing through the discharge outlet 34. An outlet 57 of the outer chamber 18 is in fluid communication with the discharge outlet 34 via the opening 54 in the flat output tap 14. Thus, the liquids in the outer chamber 18 flow out through the discharge outlet 34, through the adapter 58, and into the collection container 60 via tube 62. As such, only liquids, which are separated from solids via the filtering section 26, are continuously drained into the collection container 60. Thus, risk of the flat output tap 14, the adapter 58, and/or the tube 62 becoming clogged by solids is significantly reduced or eliminated.

Further, when the body side chamber 16 is filled with solids, or if the user desires to empty the contents in both chambers 16, 18, the flat output tap 14 can be pressed inwardly at edges 52, as shown in FIGS. 3 and 4, which opens the lip 50, which in turn opens the outlet 56 of the body side chamber 16 to empty the solids. During this process, the opening 54 may remain open, so both liquids and solids can be drained via the discharge outlet 34 of the flat output tap 14. Further, the bottom portion 46 can also be pressed on its edges to increase the size of the lumen 48 to improve draining of solids and liquids.

FIG. 6 illustrates an ostomy appliance 100 according to an alternative embodiment. Similar to ostomy appliance 10, ostomy appliance 100 includes a dual-chamber ostomy pouch 102, which includes a body side chamber for solids and an outer chamber for liquids. However, instead of the flat output tap, ostomy appliance 100 includes a fold-up type closure 104 and a liquid valve 106. Examples of such a fold-up type closures are disclosed in Villefrance, et al., U.S. Pat. No. 7,879,015, and Mandzij, et al., U.S. Pat. No. 7,879,016, both of which are commonly assigned with the present application and are incorporated herein by reference. As it was with the ostomy pouch 12, the chambers of the ostomy pouch 102 are defined by a body side wall, a center wall with a filtering section, and an outer wall. When the fold-up type closure 104 is rolled up and closed, outlets of the body side chamber and the outer chamber are closed, and the chambers are separated by the center wall. Thus, solids and liquids in stoma discharge flowing into the body side chamber are generally separated as described above with regard to ostomy appliance 10.

The outer chamber of the ostomy pouch 100 is provided with the liquid valve 106, through which the liquids in the outer chamber can be drained into a collection container (not shown.) When the ostomy pouch 102 is filled with solids, or the user desires to empty contents from both chambers, the fold-up type closure 104 can be opened or unrolled, which opens outlets of the body side chamber and the outer chamber, and both liquids and solids can be emptied together.

FIG. 7 illustrates an ostomy appliance 200 according to another embodiment. The ostomy appliance 200 includes an ostomy pouch 202 and a flat output tap 204. The ostomy pouch 202 may be any two-piece or one-piece conventional single chambered ostomy pouch. As with the flat output tap 14, the flat output tap 204 has a generally flat profile. The flat output tap 204 includes a top portion 206, which is adapted to fit in a tail portion 210 of the ostomy pouch 202, and a bottom portion 208 having a flattened cylinder-like shape. In one embodiment the bottom portion 208 has a width 222 to thickness 224 ratio of greater 2, and preferably greater than 4. As with the flat output tap 14, the flat output tap 204 is formed of a flexible, resilient material, such as silicone, rubber, elastomers, and the like.

Ostomy appliance 200 also includes a closure cap 212, which may be adapted to fit both inside and outside of an outlet end portion 210 of the flat output tap 204 to provide a two-location, leak-free seal when the closure cap 212 is engaged with the flat output tap 204. The closure cap 212 includes an outer wall 214 and a protruding insertion portion 216 arranged in the center of the outer wall 214. When the cap 212 is engaged with the tap, the insertion portion 216 is inserted into a lumen 220 of the flat output tap 204, such that the bottom portion 208 of the flat output tap 204 is positioned in a cavity 218 defined between the outer wall 214 and the insertion portion 216 of the closure cap 212. Thus, when engaged with the flat output tap 201, the closure cap 212 fits both inside and outside of the bottom portion 208 to provide the two-location, leak free seal. The closure cap 212 may be tethered to the flat output tap 204.

Figure 9:
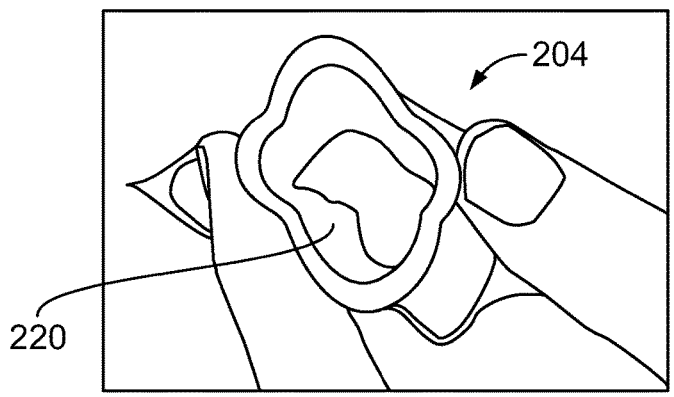
FIG. 9 is a perspective view of the flat output tap of FIG. 8 with fingers pressing edges of the flat output tap to increase a lumen size of the output tap.
Figure 10:
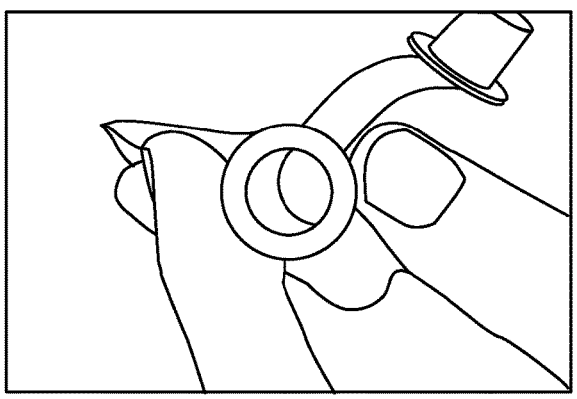
FIG. 10 is a perspective view of a conventional output tap.

As shown in FIG. 8, the flat output tap 204 includes the lumen 220, which is generally flat and has a relatively small cross-sectional thickness. Thus, flow of discharge through the lumen may be restricted. The flat output tap 204 is configured such that the flow of discharge can be manually controlled by increasing the size of the lumen 220. As shown in FIG. 9, the flat output tap 204 can be pressed on its sides to increase the flow area of the lumen 220. By controlling the amount of the pressure applied, the size of the lumen 220 can be controlled. FIG. 9 shows the lumen 220 fully opened to allow maximum flow of stoma discharge. A tube or adapter (not shown) can be connected to the flat output tap 204 for continuous draining of the discharge from the ostomy pouch 202 into a collection container (not shown.) The flat output tap 204 can provide a significantly larger lumen, when pressed open, compared to conventional cylindrical output taps, such as the output tap shown in FIG. 10. In addition, the flat output tap, which is flexible, can significantly reduce the risk of clogging. In some embodiments, the flat output tap has a lumen that is initially closed, in which the inner surfaces of the flat output tap are in contact with each other. As such the flat output tap can significantly restrict or stop the flow of stoma discharge in the closed lumen position.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. An ostomy appliance, comprising:
   a pouch, the pouch including a pouch inlet for receiving body waste from a stoma and a pouch outlet;
   a flat output tap attached to the pouch outlet, the flat output tap having at least one inlet, an outlet, and a lumen providing a path for the body waste to flow out of the pouch, wherein the flat output tap is configured such that a size of the lumen is adjustable, wherein the output tap includes a top portion configured to fit in the pouch outlet and a bottom portion, wherein the lumen is defined by inner surfaces of the flat output tap, the at least one inlet being defined in the top portion and the outlet being defined at a peripheral end of the bottom portion, and wherein the bottom portion has a flattened cylinder-like shape, and wherein a width of the bottom portion is greater than a thickness of the bottom portion; and
   a closure cap, wherein the closure cap is configured to fit inside and outside of the outlet of the flat output tap to provide a two-location, leak-free closure of the flat output tap, wherein the closure cap includes an insertion portion and a cavity defined between an outer wall and the insertion portion, wherein the insertion portion is configured for insertion into the outlet of the flat output tap and the cavity is configured to receive the bottom portion of the flat output tap when the flat output tap is closed with the closure cap.

2. The ostomy appliance of claim 1, wherein a ratio of the width to the thickness of the bottom portion is greater than 2.

3. The ostomy appliance of claim 1, wherein the pouch is a dual-chamber pouch having a body side wall, an outer wall, and a center wall including a filtering section, the body side wall, the outer wall, and the center wall being sealed together along their peripheral edges to define a body side chamber and an outer chamber, the body side chamber being defined between the body side wall and the center wall, and the outer chamber being defined between the outer wall and the center wall, wherein the body side wall includes the pouch inlet.

4. The ostomy appliance of claim 3, wherein the filtering section includes a plurality of openings, the filtering section being configured to separate solids and liquids in the body waste, wherein the liquids flow from the body side chamber through the filtering section into the outer chamber, while substantially all of the solids remain in the body side chamber.

5. The ostomy appliance of claim 4, wherein the plurality of openings are a plurality of perforations or plurality of slits.

6. The ostomy appliance of claim 3, wherein the at least one inlet includes a first inlet and a second inlet, the first inlet being configured to receive the body waste in the outer chamber and the second inlet being configured to receive the body waste in the body side chamber, wherein the second inlet is in a closed position until it is opened by a user.

7. The ostomy appliance of claim 3, wherein at least one inlet includes a first inlet and a second inlet, the output tap including a top portion arranged in the pouch outlet, the top portion including a first sealing surface, a second sealing surface, and a third sealing surface, the first sealing surface being attached to an inner surface of the outer wall proximate the pouch outlet, the second sealing surface being attached to a surface of the center wall proximate the pouch outlet, the third sealing surface being attached to an inner surface of the body side wall, wherein the first inlet is defined between the first sealing surface and the second sealing surface, and the second inlet is defined between the second sealing surface and the third sealing surface.

8. The ostomy appliance of claim 7, wherein the top portion includes a first lip and a second lip, the second sealing surface being formed on an outer surface of the first lip, the third sealing surface being formed on an outer surface of the second lip, and the second inlet being defined between the top lip and the bottom lip, wherein the first lip and the second lip are in contact with each other, such that the second inlet is in a closed position, wherein the first lip and the second lip are configured to be opened by applying a pressure along edges of the top portion, and wherein the first inlet is defined by an opening arranged between the first sealing surface and the second sealing surface.

9. The ostomy appliance of claim 8, wherein the outlet of the output tap is connected to a tube for transporting the body waste to an container, wherein the liquids in the outer chamber flow through the first inlet and are continuously transported to the container via the tube, and wherein substantially all of the solids remain in the body side chamber until the second inlet is opened.

10. The ostomy appliance of claim 9, wherein the tube is connected to the output tap via an adapter, the adapter being configured to fit in the outlet of the output tap.

11. The ostomy appliance of claim 1, wherein the output tap is configured such that a size of the lumen is increased by applying a pressure on edges of the output tap.

12. The ostomy appliance of claim 1, wherein the size of the lumen and a size of the outlet are increased by applying a pressure along the width of the bottom portion.

\* \* \* \* \*